United States Patent [19]

Dresback

[11] 4,220,153
[45] Sep. 2, 1980

[54] CONTROLLED RELEASE DELIVERY SYSTEM

[75] Inventor: David S. Dresback, Groton, Conn.
[73] Assignee: Pfizer Inc., New York, N.Y.
[21] Appl. No.: 14,388
[22] Filed: Feb. 22, 1979

Related U.S. Application Data

[63] Continuation-in-part of Ser. No. 904,049, May 8, 1978, abandoned.

[51] Int. Cl.² ............................................. A61M 7/00
[52] U.S. Cl. .................................................. 128/260
[58] Field of Search ............................. 128/155–156, 128/213, 260, 261, 222–223; 424/19, 14, 27

[56] References Cited

U.S. PATENT DOCUMENTS

| | | | |
|---|---|---|---|
| 3,005,753 | 10/1961 | Vierling | 424/15 |
| 3,846,404 | 11/1974 | Nichols | 260/230 |
| 3,946,734 | 3/1976 | Dedrick et al. | 128/260 |
| 3,948,262 | 4/1976 | Zaffaroni | 128/260 |
| 3,975,350 | 8/1976 | Hudgin et al. | 128/127 |
| 3,993,072 | 11/1976 | Zaffaroni | 128/260 |
| 3,993,073 | 11/1976 | Zaffaroni | 128/260 |
| 4,034,756 | 7/1977 | Higuchi et al. | 128/260 |
| 4,044,119 | 8/1977 | Carlson, Jr. et al. | 424/19 |
| 4,083,949 | 4/1978 | Benedikt | 424/19 |
| 4,105,779 | 8/1978 | Kobayashi et al. | 424/19 |

OTHER PUBLICATIONS

The Merck Index, 9th Ed., 1976, p. 812.
Irish Vet. J., Nov. 1974, Downey et al., 221.
Brit. Vet. J., 134, 166 (1978), Jones et al.

Primary Examiner—C. Fred Rosenbaum
Attorney, Agent, or Firm—Connolly and Hutz

[57] ABSTRACT

Delivery systems and devices for the controlled release of chemicals, including drugs, comprising a wall, formed in part at least, of a porous fabric material, pores of which contain a hydrogel, said porous wall in contact with at least a portion of a reservoir comprised of a chemical and, if desired, a water-soluble liquid excipient and/or a detergent; process for preparation thereof, and use for the controlled release of chemicals, including drugs, to an aqueous liquid-containing environment. Emphasis is given to said systems and devices in which the porous fabric material is a synthetic fabric and gelled cellulose triacetate is the hydrogel, and to their use for controlled release of drugs to animals, especially to ruminants, over prolonged periods of time.

38 Claims, 2 Drawing Figures

CONTROLLED RELEASE DELIVERY SYSTEM

CROSS REFERENCE TO RELATED APPLICATION

This application is a continuation-in-part of application Ser. No. 904,049 filed May 8, 1978 and now abandoned.

BACKGROUND OF THE INVENTION

This invention relates to improved chemical, including drug, permeable systems and devices adapted to release a drug or other chemical at a controlled rate from a drug-containing reservoir to an aqueous liquid-containing environment, particularly to an animal, including human, body environment and to drug or chemical delivery devices including such a system. It particularly relates to such systems and devices which are comprised of a wall or walls, formed in part at least, of a porous fabric, pores of which contain a hydrogel, and wherein said porous fabric is in contact with a drug or drug-containing reservoir. More particularly, it relates to boluses comprising said systems for controlled release of drugs to ruminants and which are retained in the rumeno-reticular sac of the animals.

DESCRIPTION OF THE PRIOR ART

Drug delivery systems and devices for controlled release of drugs; i.e., controlled release and sustained or prolonged release, are well known in the art. A variety of methods have been described in the literature, including physiological modification of absorption or excretion, modification of the solvent, chemical modification of the drug, adsorption of drug on an insoluble carrier, use of suspensions and implantation pellets (Edkins, *J. Pharm. Pharmacol.*, 11, 54T–66T, 1959). Other methods include mixing the drug with a carrier which is gradually disintegrated by the environment, e.g., body fluids, resulting in release of the drug. Waxes, oils, fats and soluble polymers have served as carriers.

It is also known in the art to disperse the drug throughout a solid matrix material through which the drug is released by diffusion, or to enclose the drug within a capsule having a polymeric wall or walls through which the drug can pass by diffusion (U.S. Pat. No. 3,279,996).

U.S. Pat. No. 3,975,350 describes hydrogel carrier systems comprised of polyurethane polymers for use in medicinal, pesticidal, insecticidal, algaecidal, etc. applications. The polymer, in combination with an active agent, e.g., a pharmaceutical, can be used in a variety of configurations including rods, cubes, containing the active agent within the shape or in an interior space thereof.

U.S. Pat. No. 1,693,890 describes preparation of porous membranes of cellulose acetate in the form of jellies for use in dialysis and ultrafiltration in various solvents. The process comprises precipitating the cellulose acetate from a solution thereof in acetic acid by addition of a non-solvent such as water. If desired, the membranes can be formed on a support. The membranes thus produced are impregnated with water but can be freed of water by washing with alcohol, acetone or any water miscible liquid.

Cellulosic polymer-liquid composite (PLC) materials in film, fiber or microspherical form, including cellulose esters such as cellulose triacetate or cellulose nitrate, or molecular mixtures thereof, as vehicles for the controlled release of various substances are described in U.S. Pat. No. 3,985,298. The substance to be released, including pharmaceutical agents, sweetening agents, essential oils, antiperspirants, dyes, dermatological agents, fragrances, pesticides, or fertilizers, is impregnated into and within the cellulosic PLC material as a part of or as all of the liquid phase, alcohol or water or mixtures thereof, contained within the micropores of the cellulosic PLC.

U.S. Pat. No. 3,846,404 describes semipermeable membranes of gelled cellulose triacetate useful for reverse osmosis, dialysis and ultrafiltration, and as carriers for other materials such as liquids having medicinal properties. The impregnation of smooth-finish, nonwoven polyethylene fabric and plain cotton cloth with gelled cellulose triacetate to provide supported cellulose triacetate hydrogel materials is described. The biomedical use of gelled cellulose triacetate bandages and dressings impregnated with various types of medication and the use of medication-impregnated gelled cellulose triacetate products as animal implantable slow-release agents are described, as is the casting of gelled cellulose triacetate onto a woven or nonwoven supporting sheet material.

Controlled release drug delivery devices comprising a reservoir formed of a drug and a solid or liquid drug carrier and, in contact with or surrounding the reservoir, a wall formed of any of a variety of materials, including a microporous material the micropores of which contain a diffusive medium (e.g., a liquid phase comprised of a solution, a colloidal solution, a suspension, or a sol) permeable to passage of drug by diffusion, are described in one or more of the following U.S. Pat. Nos. 3,993,072; 3,993,073; 3,896,819; 3,948,254; 3,948,262; 3,828,777; 3,797,494; 4,060,084 and 3,995,634.

U.S. 3,993,072; 3,948,254 and 3,993,073 describe various materials suitable for the wall including cellulose triacetate. The latter patent also discloses hydrophilic hydrogels of esters of acrylic acid and methacrylic acid, and cross-linked polyvinyl alcohol as suitable wall forming materials. A key feature of the devices of these patents is the use of a wall, composed in part at least, of a microporous material, pores of which contain a drug release rate controlling medium permeable to passage of drug, and a reservoir comprising drug plus a carrier which is permeable to passage of drug but at a higher rate than the permeability of the rate controlling medium housed in the pores of the microporous wall. Devices suitable for administering therapeutic or nutrient substances to ruminants and which comprise encasing the substance in a permeable, water-soluble material having capillaries or interconnecting pores extending through them and paper or cloth partially impregnated with water-insoluble polymers, e.g. cellulose acetate, are described in British Pat. No. 1,318,259.

U.S. Pat. No. 3,594,469 issued July 20, 1971 describes pellets containing magnesium and iron for administration to ruminants for supplying the ruminants with said metals over an extended period of time. In one embodiment, the pellet consists of a cylindrical tube of magnesium alloy filled with shot (to achieve specific gravity of at least 2.2) and some biologically active substance and plugged at both ends by porous discs.

British No. 1,098,006 describes sustained-release pharmaceutical compositions in the form of coated pellets or tablets which contain a pharmaceutically active ingredient soluble in fluids of the gastrointestinal tract and wherein the coating layer comprises one or more areas impermeable by the fluids and by the pharmaceutically-active ingredient, and one or more other areas provided by a dialysing membrane permeable by the fluids and by the pharmaceutically-active ingredient and through which the ingredient gradually diffuses when the tablet is administered. One form of the pellet or tablet comprises a rigid non-diffusible plastic jacket or shell which encloses the pharmaceutically-active ingredient within a central hollow chamber, e.g. a tube, the ends of which are sealed by the dialysing membrane. Alternatively, the pellet or tablet may comprise a non-toxic rigid non-diffusible plastic body of polymethylmethacrylate or polytetrafluoroethylene having a plurality of passages extending from the center of the body outwardly to the surface, and which accomodate the pharmaceutically-active ingredient, the outer ends of the passageways being sealed by the dialysing membrane.

U.S. Pat. No. 3,938,515 makes known devices designed for continuous administration of a drug for a prolonged period comprising a reservoir containing the drug and a carrier permeable to the drug, and a wall surrounding the reservoir which is permeable to the drug, but at a rate less than that of the carrier. The wall is formed of various polymers including polyethylene, polypropylene, ethylene/propylene copolymer, cellulose acetate, ethyl cellulose, cellulose acetate butyrate, cellulose nitrate and cellulose acetate propionate. The drug carrier can be a solid such as a hydrophilic hydrogel of acrylic acid esters, gelatin or a liquid such as ethylene glycol, emulsions of gum arabic and water. Hydrophilic hydrogel carriers are also described in U.S. Pat. No. 3,993,072 and U.S. Pat. No. 3,948,254.

A further device for controlling the release of a biologically active substance is described in U.S. Pat. No. 3,946,734. The device, a diffusion cell, designed principally for use as an implant, is essentially a capillary, one end of which is sealed with an impervious material and the rest of the tube and the other end thereof is sealed with a porous, neutral hydrogel. The biologically active substance is placed in the capillary against the impervious material and the capillary then filled with the hydrogel, i.e., a neutral hydrophilic polymeric gel through which the biologically active medicament will diffuse. A polymeric material such as cellulose may be placed across the opening above the neutral hydrophilic polymer, if desired, to limit access into the capillary of certain body constituents. Typical materials for use as the neutral hydrophilic polymeric gel are agarose and polyacrylamide.

U.S. Pat. No. 3,896,806 describes implants for directed infusion of biologically active substances having, as one component, a cup shaped membrane formed from a dried hydrogel (e.g., copolymers of glycol methacrylate or acrylate) and advantageously reinforced with a fabric.

Many of the prior art controlled release devices are described as zero order release devices. However, said devices are able to maintain zero order rates of release for relatively short fractions of their projected life span and are not practical for extended use as, for example, in ruminants. The devices of this invention, on the other hand, achieve and maintain controlled, predictable, zero order rates of release of a given drug for extended periods of time. Additionally, the prior art devices, including those comprising a drug-containing reservoir surrounded by a shaped wall formed at least in part of a microporous material, pores of which have a drug release rate controlling medium (diffusive medium) permeable to passage of drug, are subject to physical clogging or physical damage in certain use environments such as the rumeno-reticular sac of ruminants. The clogging decreases and even stops release of the drug rendering the devices inoperative for their intended purpose. The devices of this invention wherein pores of the porous material in contact with the drug-containing reservoir contain a hydrogel are essentially free of this problem and able to provide controlled and predictable release rates of drug to an aqueous liquid-containing environment for extended periods of time.

When used for controlled releawe of highly water-soluble drugs, prior art devices (of the type described in U.S. Pat. Nos. 3,993,073; 3,993,072; 3,967,618; 3,948,262; 3,948,254 and 3,896,819) prefer that the wall and/or the reservoir be formed from a material that is substantially impermeable to water in order to prevent dilution of the drug in the reservoir by absorption of body fluids into the device and decrease in drug release rate. They are, therefore, not suited for delivery of water soluble drugs, especially at relatively high rates. Further, the devices described in most of these patents require that the permeability to drug of the drug release rate controlling medium in the micropores of the microporous wall surrounding the reservoir be less than the permeability of the liquid carrier in the reservoir to the drug. By this means, passage of drug through the wall is the rate controlling step. The devices of the present invention are completely free from such restrictions. In fact, a significant difference of the herein-described devices over the prior art devices resides in the presence of highly water permeable hydrogel in the pores of the porous material in contact with the reservoir. Said devices depend upon diffusion of water from an aqueous-liquid environment into which the device is placed through liquid filled pores or channels in the hydrogel and into the reservoir, and the outward diffusion of drug from the reservoir to the environment. Unexpectedly, the concentration of dissolved drug in the reservoir does not diminish, resulting in a substantially constant rate of release for a prolonged time. However, the amount of drug dissolved in the reservoir varies continuously throughout the life span of the devices of this invention.

The use of a low-level of the anthelmintic agent morantel tartrate in the drinking water of calves, the calves having continuous access to the medicated water, as a means of endoparasite control is reported by Downey et al., Irish Vet. J. 221, November, 1974 and in British Pat. No. 1,530,161. Continuous anthelmintic medication of calves from early April to mid-July was found to suppress worm-egg output by the calves and to prevent, or at least minimize, development of heavy larval infection on herbage.

Daily low-level feed administration of morantel tartrate to calves from turning out to mid-July was found by Jones et al., Brit. Vet. J. 134, 166 (1978) to successfully control parasitic gastroenteritis and lungworm infections by reducing contamination of the pasture available to the grazing calf.

SUMMARY OF THE INVENTION

The present invention relates to improved chemical, including drug, permeable systems and devices adapted to release said substances at a physiologically or pharmacologically effective controlled rate from a chemical-containing reservoir to an aqueous liquid-containing environment, particularly to an animal, including human, body environment. In particular, it relates to such systems and devices comprising a container, at least part of the wall or walls of which comprise a porous fabric material, pores of which contain a hydrogel, and to devices wherein said porous fabric material is in contact with at least a portion of a chemical or a chemical-containing reservoir. More particularly, it relates to boluses comprising said systems for controlled release of drugs to ruminants and which are retained in the rumeno-reticular sac of the animals.

The improved chemical, including drug (the terms are used interchangeably herein), permeable systems and devices of this invention are of value for controlled release of drugs and other chemicals to aqueous liquid-containing environments and are of particular value for oral dosing of animals, including man, and can be used for a variety of drugs. In addition, the devices are particularly well suited for delivering highly water soluble substances at high rates, not readily achievable with prior art devices. The systems and devices of this invention provide for the controlled release of chemicals over a prolonged period of time, are easy to produce and are reliable and easy to use. Moreover, the devices described herein maintain their physical and chemical integrity, do not clog in the environment of use and are especially valuable for oral use in a bolus-shaped form for ruminant animals. They provide, for the first time, a practical device for controlled and continuous release of chemicals, including drugs, to an aqueous liquid-containing environment and, therefore, fill a long-existing need, particularly in animal husbandry.

The controlled rate release systems and devices of this invention comprise a barrier or wall in contact with at least a portion of a chemical-containing reservoir and wherein the wall consists partly or entirely of a porous fabric material, pores of which contain a hydrogel permeable to passage of liquid from the environment through pores within the hydrogel itself and of chemical from the reservoir by diffusion. When the devices of this invention are in use, the hydrogel contains liquid from the environment, said liquid being contained within areas or channels (pores) within the hydrogel itself and which serve as pathways for diffusion of environmental liquid and transport of drug.

The systems and devices of this invention can assume a wide variety of shapes and sizes subject to the purpose for which they will be used. They can, for example, be capsule-shaped for oral use in humans and animals or cylindrical for implant or for use as a bolus in ruminants.

A favored form of device of this invention, in its broadest aspect, comprises a porous fabric material, pores of which contain a hydrogel permeable to passage of liquid from the environment and of drug by diffusion through pores within the hydrogel, said porous fabric material in contact with at least a portion of a chemical, including drug, containing reservoir comprising chemical and, if desired, a suitable water-soluble liquid excipient and also, if desired, a detergent, said device being made in the form of a bolus for use in the controlled release of drug to ruminant animals, especially cattle and sheep, for a prolonged time. Particular use of such boluses is for parasitological, especially helminthic, control, prophylactic and therapeutic, of gastroenteral and lungworm infections in cattle and sheep and of helminth contamination of pasture land. The term "bolus" as used herein includes devices which are generally cylindrical, spherical, spheroidal, elliptical, or other form which are free of sharp edges and protuberances.

The prior art devices require consideration and compromise of several factors for each use; namely, the carrier used in the reservoir; the solubility and/or permeability of the carrier to the drug contained in the reservoir; the nature of the microporous wall surrounding the reservoir; the diffusive medium contained in the pores of the microporous wall; the relative permeability rates of the diffusive medium and carrier to the drug; the relative solubilities of the drug in the diffusive medium and carrier; and the need for maintaining a substantially constant amount of dissolved drug in the reservoir.

The devices of the present invention, on the other hand, are far simpler in design and operation. For a given device, the release rate of chemical can be varied widely by the simple expedient of varying the area of thickness of porous material, pores of which are filled with hydrogel, in contact with the reservoir. Thus, manipulation of only two parameters permits control of the amount of chemical released.

BRIEF DESCRIPTION OF THE DRAWINGS

The drawings are not drawn to scale but are merely set forth to illustrate various embodiments of the invention.

DETAILED DESCRIPTION OF THE DRAWINGS

Figure 1:
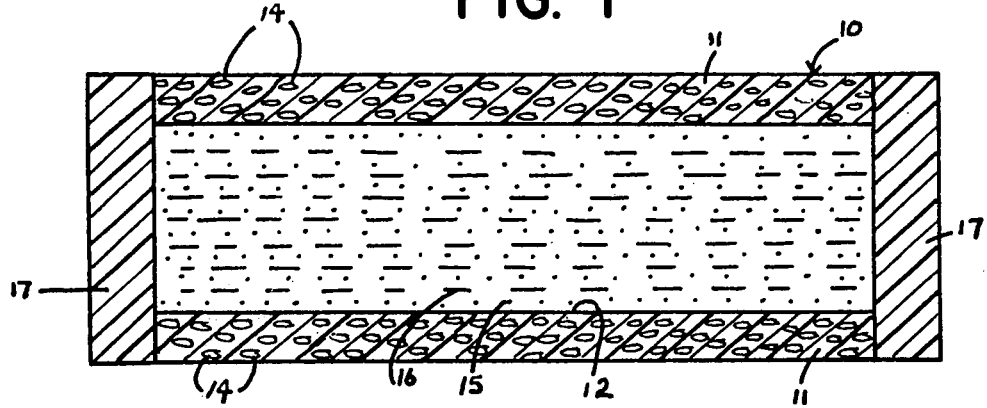
FIG. 1 is a perspective, cross-sectional view of a delivery device of this invention depicting a hydrogel impregnated cylindrical porous wall in contact with a drug-containing reservoir wherein the end walls are comprised of non-permeable material.
Figure 2:
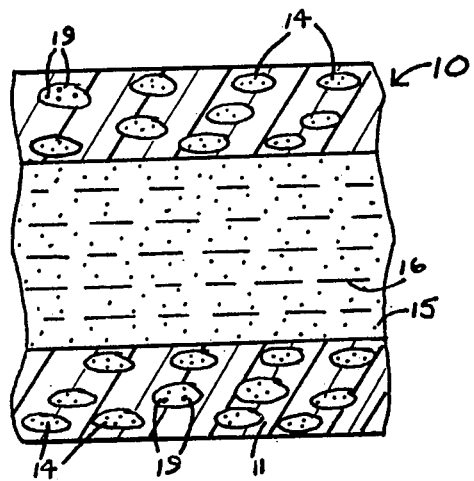
FIG. 2 is an enlarged cross-sectional view of a delivery device of this invention illustrating hydrogel filled pores of a porous wall in contact with a chemical-containing reservoir.

FIGS. 1 and 2 illustrate examples of devices according to this invention. The fact that few examples are illustrated is not to be construed as limiting the invention, many variations and equivalents of which are possible. In FIG. 1, delivery device 10 is comprised of a cylindrical wall 11 in contact with a chemical-containing reservoir 12. Wall 11 is formed of a porous fabric material, pores 14 of which contain a hydrogel (not indicated) through which liquid from an aqueous liquid-containing environment diffuses into reservoir 12 and chemical from the reservoir diffuses into the environment through channels or pores within the hydrogel itself. Reservoir 12 is comprised of a chemical 15 and, in a preferred embodiment of this invention, of a drug and a water-soluble excipient 16.

FIG. 2 presents an enlarged view of a porous wall 11 of a device 10 of this invention, pores 14 of which contain a hydrogel 19, in contact with a chemical-containing reservoir 12 comprised of a chemical 15 and a water-soluble liquid excipient 16.

In addition to the devices described and illustrated herein, prior art devices such as are described in J. Pharm. Sci. 66, 159–162 (1977) and which consist of a non-permeable cylinder enclosing a reservoir and having a slot-like port running its entire length and which communicates with the reservoir, are improved by placing a porous fabric material, pores of which are filled with hydrogel, over or in the slot so as to minimize clogging of the slot when the device is in use.

DETAILED DESCRIPTION OF THE INVENTION

As illustrated above, the improved delivery devices or systems of this invention have a chemical, including drug, containing reservoir comprising a chemical and, in a preferred form, chemical and a water-soluble liquid excipient. The water-soluble liquid excipient serves several important functions, such as elimination of air from the reservoir, thus permitting greater "loading" in the manufacture of the devices and enhancement of convective mixing within the reservoir (which assures constant rate of chemical release). Additionally, said water-soluble liquid excipient serves a still further role in that, as chemical dissolves, there is no apparent volume change as the chemical goes from the solid or crystalline state to the solution state. Typical water-soluble liquid excipients include mono-and polyols and ethers thereof, such as ethanol, ethylene glycol, propylene glycols, glycerol, polyethylene glycols, sorbitol, di- and triethylene glycol, di- and tripropylene glycol, 1,2-dimethoxyethane, mono-$C_{1-4}$ alkyl ethers of ethylene and propylene glycols; N,N-dimethylformamide, dimethylsulfoxide, and the like. The excipients must, of course, be compatible with the fabric and hydrogel.

Of course, when the herein-described devices are to be used for animals, including humans, or in aqueous liquid-containing environments used by animals, e.g. aquariums, fish ponds, animal and poultry water supplies, hydroponic systems, the water-soluble liquid excipient should be a physiologically acceptable substance.

The amount of water-soluble liquid excipient used per unit weight of drug depends upon the characteristics of the drug. In general, sufficient excipient is used to permit formation of the drug-excipient combination into a compact mass, and is readily determined by simple experiment.

Detergents, up to 20% by weight, based on the total weight of the reservoir (chemical, including drug, plus, if used, excipient and detergent) can be used in the reservoir to minimize possible clogging of the devices when in use. Representative detergents can be inorganic or organic in nature and include sodium and potassium hexametaphosphates and tripolyphosphates, sodium lauryl sulfate, sodium glyceryl monolauryl sulfate, dioctyl sodium sulfosuccinate, bis(1-methylamyl)sodium sulfosuccinate, polyoxyethylene sorbitan mono-oleate and other fatty acid esters, and others known to those skilled in the art. The amount of detergent when one is used is not critical and, in any instance, is kept to a minimum in order not to sacrifice loading of chemical into the reservoir. The optimal amount is determined by procedures described below.

In this specification and accompanying claims, the terms "reservoir", "chemical-containing reservoir", and "drug-containing reservoir" are used interchangeably. For convenience, since the preferred devices of this invention are those used for controlled release of drugs, the term "drug-containing reservoir" is the favored term.

The porous fabric materials used can be isotropic, i.e., of homogeneous pore structure throughout the cross-section of the material, or can be anisotropic, i.e., of non-homogeneous pore structure. They should, of course, be insoluble and non-reactive with the environment and with the contents of the reservoir. In general, porous fabric materials having pore sizes of from about one micron to about 100 microns can be used in the controlled release devices of this invention. In order to facilitate transfer of the drug from the reservoir to the environment when the controlled release devices of this invention are used, the pores, or a portion of the pores, of the porous fabric material are filled with a hydrogel. The net result of the combination of the porous fabric material, pores of which are filled to a greater or lesser extent with a hydrogel, is provision of a device able to withstand clogging and physical destruction under conditions of normal use and, by maintaining its physical integrity, one which can be used in environments and situations under which previously known hydrogel devices would be destroyed and ineffective for controlled release of drugs over prolonged periods of time. The herein described devices are of particular value for use in ruminants, especially in cattle and sheep. The hydrogel-containing pores permit passage of liquid (water) through pores within the hydrogel itself by diffusion from the environment into which the controlled release device is placed when in use into the reservoir dissolving the drug. The drug then diffuses through liquid in pores of the hydrogel-containing pores of the porous fabric material barrier at a rate dependent on the drug concentration in the solution in the reservoir, upon the resistance offered by the barrier; i.e., liquid in the pores of the hydrogel, and the effective surface area of the porous portion of the wall.

As drug leaves the device, a zone of depletion gradually forms giving rise to a moving drug/solution boundary. The diffusion of water into the device from the environment through pores within the hydrogel-containing pores of the wall into the reservoir gives rise to convective mixing of the incoming aqueous phase with the solution in the reservoir of the device. The motive force for this mixing is the difference in densities of the two solutions caused by their large concentration differences. A function of the water-soluble liquid excipient, as noted above, is to help maintain this large density difference, hence enhancing this critical mixing. The convective mixing results in a constant drug concentration within the reservoir which in turn provides controlled release of the drug over a prolonged period of time, thus insuring zero order release of drug as long as undissolved drug remains in the device. As drug is removed from the reservoir, and aqueous liquid from the environment diffuses into the reservoir, the amount of dissolved drug within the reservoir varies continuously throughout the life span of the device; that is, throughout the prolonged time period of drug release. This mechanism of drug release allows any device geometry to be adopted, the size and shape of the reservoir is not limited. This is in direct contrast to the prior art devices of U.S. Pat. No. 3,993,073 which depend upon, and are so fabricated as to achieve, a substantially constant amount of dissolved drug within the reservoir, diffusion of dissolved drug within the reservoir to supply drug to the wall, and, therefore, have severe product limitations in terms of size and shape.

The term "hydrogel" as used herein refers to a gel having water content and is defined in Hackh's Chemical Dictionary, Fourth Edition, Grant, page 322, 1969, as "a gel produced by the coagulation of a colloid with the inclusion of water". Representative hydrogels which can be used to fill the pores of the porous fabric material are the following: gelled cellulose triacetate (see U.S. Pat. Nos. 1,693,890 and 3,846,404), cellulose acetate hydrogels having an acetyl content of from 20% to 40%; polymeric hydroxyethyl methacrylate; cross-bonded polyvinyl alcohol; agarose; polyacrylamide; cross-linked partially hydrolyzed polyvinylacetate, hydroxyethyl acrylate, diethylene glycol monoacrylate, diethyleneglycol monomethacrylate, 2-hydroxypropylacrylate, 2-hydroxypropyl methacrylate, 3-hydroxypropyl acrylate, 3-hydroxypropyl methacrylate, dipropylene glycol monomethylacrylate, vinylpyrrolidone, acrylamide, methacrylamide, N-propylacrylamide, N-isopropylmethacrylamide, N-methylacrylamide, N-2-hydroxyethylmethacrylamide; polyurethane hydrogels comprising lightly cross-linked polymers of isocyanate terminated prepolymers which are the reaction product of a poly(alkyleneoxy)polyol with an organic diisocyanate lightly cross-linked with water or an organic polyamine, as described in U.S. Pat. No. 3,939,105; copolymers of ethylenically unsaturated monomers of hydroxyalkyl acrylates and methacrylates, and of alkoxy alkylene glycol acrylates and methacrylates, as described in U.S. Pat. No. 4,038,264; polyether polyurethane resins produced by reaction of an organic diisocyanate with a mixture of at least two diols, one of which is a water-soluble polyalkylene glycol with molecular weight of from 3,000 to 30,000 and the second of which is an oxyalkylated diphenol having from 2 to 20 oxyalkylene groups, and others as are known to those skilled in the art.

Favored hydrogels for use in this invention are polyurethanes, polymeric hydroxy lower alkyl acrylates or methacrylates, vinyl pyrrolidone, acrylamide, N-lower alkyl acrylamides, and methacrylamides, especially those cross linked or copolymerized with a hydroxyalkyl acrylate or methacrylate to render the resulting copolymer water insoluble. The preferred hydrogels are gelled cellulose triacetate, polymeric hydroxyethyl methacrylate, and cross-bonded polyvinyl alcohol. Especially preferred is gelled cellulose triacetate which affords smooth and efficient operation of the controlled release devices described herein.

The water present in the pores of the hydrogel can be readily replaced by water-soluble liquids such as the water-soluble liquid excipients disclosed above. Other water-soluble liquids can also be used to replace the water, including alcohols having one to four carbon atoms. As a practical matter, in order to stabilize the devices of this invention, particularly when the hydrogel is gelled cellulose triacetate, the water of the hydrogel is replaced with a suitable water-soluble liquid which has a vapor pressure lower than that of water so the devices can be stored without loss of efficiency as a result of drying out of the hydrogel. When a water-soluble liquid excipient-drug combination is used in the reservoir, it is convenient to use the same liquid to replace the water from the hydrogel.

The hydrogels themselves are porous in the sense they contain areas or regions, i.e., channels or pores, filled with water or other liquid.

It is, therefore, intended throughout this specification when referring to diffusion or transport of chemicals or drugs through walls, "pores of which contain a hydrogel", or similar expression, to mean that diffusion or transport, of the chemical or drug occurs via these regions rather than through the hydrogel per se. The hydrogel itself has liquid filled pores which serve as the diffusion pathways, and, in effect, is considered as being permeable to passage of environmental liquid and of chemical from the reservoir.

The porous wall in contact with the drug-containing reservoir can be any of a variety of fabrics, synthetic or natural. The term "fabric" as used herein refers to any material woven or knit from fibers, natural or synthetic, including metal fibers. The porous material can completely surround the reservoir or can comprise only a portion of the wall surrounding the reservoir. Suitable fabrics are polypropylene and polyethylene, especially those fabrics of each type commonly referred to as "filter cloth", glass, poly(tetrafluoroethylene), nylon, cotton, modacrylic fibers; i.e., acrylic fibers composed of a long chain synthetic polymer containing 35–85% of acrylonitrile units; acrylic fibers; i.e. synthetic polymers having a minimum of 85% acrylonitrile by weight; polyesters; i.e., a long chain synthetic polymer composed of at least 85% by weight of an ester of a dihydric alcohol and terephthalic acid; poly(vinyl acetate), poly(vinyl chloride), poly(vinyl acetate-co-vinyl chloride), poly(vinyl alcohol), poly(vinyl alcohol-co-vinyl acetate), poly(vinyl alkyl ethers); polymers of vinylidene cyanide, vinylidene chloride, vinylidene fluoride; polyureas and others known to those skilled in the art [see *Encyclopedia of Polymer Science and Technology*, Vol. 1, 342 (1964); Vol. 8, 812 (1968); Vol. 9, 403 (1968); Vol. 10, 347, 206 (1969); Vol. 6, 275 (1967); Vol. 11, 62, 445, and 506 (1969); Vol. 14, 305,575 (1971), Interscience Publishers, New York]. Additionally, metal screens or filter cloths including those fabricated from stainless steel, carbon steel, brass, copper, aluminum, various alloys such as nickel-copper, etc., are suitable.

The particular fabric chosen must, of course, be compatible with the hydrogel with which it is to be impregnated and with the end use of the device. Thus, for a device to be used as a bolus for administering a drug to ruminants over a prolonged period of time, cotton would not be used as the fabric since it would undergo degradation by the ruminant. In a device to be used for controlled release of a chemical to an aqueous environment such as an aquarium or a reservoir, cotton can be used.

Nylon would not be used as the fabric when gelled cellulose triacetate is to serve as the hydrogel since it would be degraded by the formic or acetic acid used during the impregnation process.

The hydrogel impregnated porous fabric materials must, of course, be of sufficient strength, durability and inertness to drug and the use environment so that the controlled release device produced therefrom retains its physical and chemical integrity throughout its entire life.

The porous fabric material is impregnated with an appropriate hydrogel by procedures known to those skillled in the art, as, for example, by impregnating the fabric with the hydrogel from both sides using a roller to force it into the pores. When the hydrogel is gelled cellulose triacetate, a solution of cellulose triacetate in formic acid or preferably acetic acid is forced into the pores of the porous fabric material as described. Following impregnation, the cellulose triacetate "loaded" fabric is then contacted with and equilibrated with a large volume of water to produce the hydrogel impregnated fabric material.

When the hydrogel is derived from 2-hydroxyethyl methacrylate cross-linked with ethylene glycol dimethacrylate as described in U.S. Pat. No. 3,520,949, impregnation of the porous fabric material is accomplished by filling its pores with the 2-hydroxyethyl methacrylate—ethylene glycol dimethacrylate mixture and then polymerizing the mixture within the pores by addition of a free radical catalyst such as t-butyl peroctoate. In like manner, other hydrogels, are impregnated into the porous wall material by such "in situ" procedures from appropriate reactants. When the hydrogel is cross-linked polyvinyl alcohol, the pores are filled with polyvinyl alcohol (10% aqueous solution)—resorcinol (2–3%) mixture by procedures described herein and the cross-linking is accomplished in situ. Other cross-linking agents can, of course, be used as is known to those skilled in the art.

For production of devices stable to storage prior to use, the hydrogel filled pores are freed of water by allowing them to equilibrate in a suitable water-soluble liquid such as, for example, the water-soluble liquid excipients enumerated above. It is, as noted, convenient to exchange the water in the hydrogel-filled pores of the porous wall material with the same water-soluble liquid used as excipient in the reservoir when the reservoir comprises a chemical-excipient combination. If chemical alone comprises the reservoir of the herein described devices, the choice of water-soluble liquid used to replace water from the hydrogel in the hydrogel-filled pores of the porous wall is determined only by the end use of the device; i.e., whether a physiologically acceptable water-soluble liquid is required. Such a liquid is conveniently placed in the hydrogel at the time of preparing the porous wall, pores of which contain a hydrogel, prior to filling the reservoir of the device as is illustrated herein.

The prior art devices most closely related to the devices of this invention; i.e. those of U.S. Pat. Nos. 3,993,073 and 3,993,072 depend upon different permeability rates of drug through a medium contained in the pores of the porous wall relative to that of drug in the drug-carrier phase in the reservoir. In order to achieve the zero order release rate alleged for the devices described in said patents it is essential that the medium in the walls of the devices have a lower permeability to drug than does the drug carrier within the reservoir. The medium in the wall thus becomes the drug rate of release controlling portion of the device.

Dissolved drug diffuses through the more permeable carrier to the inner wall fast enough such that the wall becomes the drug rate of release controlling portion of the device. This results in zero order release rates for some time until the receding drug boundary in the device becomes large enough to offset the difference in permeabilities between carrier and wall medium, then zero order rates are no longer achieved. Because of this, successful practical use of these devices is limited and they are not suitable for zero order delivery of large amounts of drugs in practical, useful dosage form shapes.

The devices of the present invention, contrary to the prior art devices, when in use, have aqueous environmental medium in the wall medium as well as in the reservoir. Although permeability to the drug is the same in the liquid in the wall and reservoir, zero order release rates are attained for large fractions of the total device lifetime. In addition, maintenance of zero order release does not depend upon diffusion in the reservoir carrier, thus there are no geometric or dose restrictions on these devices and for the first time large amounts of drugs can be delivered at zero order rates in embodiments of practical sizes and shapes.

For most efficient operation of the controlled release systems and devices of this invention, to reduce leaking and clogging, it is important that the porous fabric material be impregnated with hydrogel as completely as possible. Devices of the same surface area can, by varying the characteristics of the membrane wall, especially its thickness, pore size, and porosity and by varying the size of the load in the reservoir, provide different dosage rates and release periods for a given drug.

As noted above, a preferred form of device of this invention is that of a bolus for use in controlled release of a drug to ruminant animals, principally to cattle and sheep, for a prolonged period. The bolus is administered to the ruminant in such a manner, preferably by oral administration, that it remains in the rumeno-reticular sac for an extended period of time, during which period it continuously releases drug to the animal at a controlled release rate. Said devices thus permit control (prophylactic and therapeutic) of various pharmacological and physiological conditions to which the animals are subject by simple oral administration to the animals of said devices.

In order that the bolus, once introduced into the rumeno-reticular sac of cattle, remain there for an extended period, it is necessary that the bolus have a density of at least 2.0 g./ml. In practice, the density can range from as low as 2.0 to as high as 7, or even greater. Density, of course, is the most significant factor affecting retention of the bolus in the rumeno-reticular sac. Overall size of the bolus is a function of the needed dose to be given and size that can be practically administered. Based on this, once the desired size is determined, additional weight can be added to achieve desired average density. If possible, it is desirable to use maximum allowable size since larger boluses of a given density are better retained than those of lower density. However, when the average density of the bolus increases to a value greater than about 5.0, an increase in size of the bolus does not significantly improve the retention factor. The favored average density range for the bolus is from about 2.5 to about 5 g./ml.

The size of the bolus, of course, depends upon the animal to be treated therewith. For ruminants such as sheep and goats, the bolus size and weight will be less than that required for cattle. The maximum size of bolus for use in any animal is determined by the practical difficulties of administering such an object to the animal.

For administration to sheep, the minimum weight of bolus having a density of 4 which will be retained is about 1 gram. The size of a bolus will vary according to the density of the bolus. For administration to cattle, the minimum weight of bolus having an average density of 4 is about 5 grams. Again, as noted above, the upper limits of size are determined by the practical convenience of dosing the animal in question and by the minimum average density of the bolus. For example, a bolus of about 7.5 centimeters in length by 2.5 centimeters in diameter and having a density of 2.2, will have a weight on the order of about 90 grams.

The density of boluses comprising only the elements enumerated above is generally below the lower level set forth above. It, therefore, becomes necessary to increase the average density of the bolus by incorporation of a suitable high density material such as a metal (iron powder, iron shot, steel shot) or other densifiers, minerals such as $CaSO_4$, to increase the density to the desired value. The average density can be conveniently increased by fabricating the bolus from a metal (steel, iron, alloy) tube and placing the hydrogel impregnated fabric over the ends of the tube. Alternatively, it can be accomplished by incorporating into the bolus, as an inner sleeve, a high density, perforated material, e.g. a metal (such as stainless steel, steel, especially low carbon steel, or iron) which, in turn, is surrounded by the hydrogel impregnated porous fabric material. The perforations in the sleeve should be sufficiently large so as to permit free passage of drug, and liquid from the environment, through the hydrogel impregnated porous fabric material. The principal functions of such a tube or sleeve are to increase the average density of the bolus to a value such that the bolus is retained in the rumeno-reticular sac and to regulate the surface area of the hydrogel impregnated porous fabric material in contact with the drug-containing reservoir. In addition, such construction, although not necessary, also improves the physical stability of the bolus, ensuring that its physical form is substantially retained under conditions of use. A still further, and preferred, alternative comprises a bolus comprising a metal, steel or iron, cylinder, one or both ends of which are capped with a porous fabric material, pores of which are impregnated with a hydrogel. Boluses of this type are preferred because of their simplicity and economy of manufacture and the ease with which their density can be adjusted. A low carbon steel is highly favored as construction material for the cylinder. Further alternatives comprise a bag, a packet or envelope shaped device fabricated from the hydrogel impregnated fabric, suitably closed, which contains the chemical, and/or water-soluble excipient, and/or detergent. Such devices are simple and economical to produce and are ideally suited for a great many uses, especially in treating water supplies and in pisciculture. They offer a maximum surface area and thus permit fabrication of devices capable of controlled release of chemicals over an extremely wide range. Other alternatives will suggest themselves to the man skilled in the art.

The controlled release devices of this invention can be used for a variety of purposes and situations wherein controlled release of a drug or other chemical is desirable. They can be used for administering drugs and providing chemicals at sites near to or remote from the point of application of the device. They can be positioned by appropriate means in suitable locations within the animal body where they are in contact with body fluids, e.g., the stomach of farm animals, especially the rumeno-reticular sac of ruminants. Also included within the controlled release devices of this invention are those for use as depot implants for the purpose of administering a drug at a controlled rate to the host. The implants differ from devices of this invention for other purposes only in their shape which is, of course, adapted for implantation. Other uses includes sulingual or buccal tablets, pessaries, suppositories, bandages and skin patches. Still other uses for the controlled release systems and devices of this invention occur in agriculture for administration of fertilizers and pesticides, in pisciculture including aquariums and fish ponds; in drainage ditches, canals and tanks as for control of algae; and in water supplies especially for animals and poultry in need of drugs for therapeutic or prophylactic treatment.

The criterion for suitable substances, drugs or chemicals, for use in the devices of this invention is that they be sufficiently soluble in water to achieve a rate of release of said drug or chemical in the use environment which will produce the desired result. For this reason, drugs and chemicals which are acids or bases, are desirably used in the form of their physiologically or pharmacologically acceptable salts. The rate of release of drug, or chemical, from the herein-described devices is dependent upon several factors such as the thickness of the wall, available surface area, effective pore diameter, porosity of the wall, the nature of the hydrogel, the concentration of the substance in the reservoir, and the solubility thereof in the environmental liquid. The suitability of a given substance is determined as is described below.

Representative of the drugs which can be used in the devices described herein are the following: anthelmintics, including salts of morantel, pyrantel, oxantel, piperazine, diethylcarbamazine, levamisole, tetramisole, and hygromycin B; antibacterials including salts of tetracyclines, such as 5-oxytetracycline, chlorotetracycline, doxycycline and Mannich bases thereof; penicillins such as ampicillin, penicillin G; aminoglycosides such as neomycin, streptomycin, apramycin, bacitracin as its zinc or methylene disalicylic acid derivative; macrolides such as erythromycin, oleandomycin and tylosin; antibacterial growth promotants such as salts of avoparicin, polymyxin, lincomycin, bambermycin and efrotomycin; hormonal growth promotants including diethylstilbestrol, zearalanol and melengestrol acetate; antiparasitic agents such as amprolium; nutritional agents such as soluble salts of magnesium, selenium, copper, and vitamins such as thiamine hydrochloride; sulfa drugs such as sulfamethazine; molluscicides such as N-tritylmorphine; and bloat prevention agents such as alcohol ethoxylates and poly(oxyethylene)-poly(oxypropylene)-poly(oxyethylene)polymers, e.g. poloxalene.

As noted above, the drug-containing reservoir, in a preferred form of this invention, comprises a drug and a water-soluble excipient. Devices so constructed have the advantage of offering a greater amount of drug per device and of extending the useful life of the device. However, the reservoir can contain only the chosen drug.

The devices of this invention are especially valuable as long-acting boluses for control (therapeutic and prophylactic) of helminth infections in ruminants, cattle in particular. Protection of range animals becomes relatively convenient. In temperate climates, the low, early spring population of pasture infective larvae, the residue of the previous season's contamination, is multiplied by cycling through animals grazing thereon to produce, in the summer, a sharp increase in pasture infectivity. This condition gives rise, during the summer grazing season, to clinical parasitism and performance depression of the animals grazing on said pasture.

The continuous and controlled release of anthelmintic agent, e.g., morantel, in the rumeno-reticular sac of grazing animals early in the season when pasture contamination is low suppresses helminth egg and subsequent larval output and thus breaks the above-mentioned cycle and keeps the pasture and animal worm burden at a low level. Parasitic infections of ruminants grazing on the same pasture land during the summer season is thus minimized. This method of helminth control is especially attractive and valuable for calves since they are highly susceptible to helminths when first placed on pasture. Consistent use of boluses reduces the reservoir of infective helminth forms at a given location. Utilization of anthelmintic-containing boluses of this invention in this manner prevents, or at least minimizes, the seasonal increase in pasture larvae which causes parasitic gastroenteritis and performance depression in grazing animals later in the season. In this mode of control the period of drug release is that of the spring multiplication phase, not the period of heavy pasture contamination, larval challenge and worm infestation which produces clinical disease and performance depression. It is for this reason that this mode of usage is called "indirect control". To put it another way, the grazing of ruminants having in their rumeno-reticular sac one or more of the herein-described devices, which device permits controlled and continuous release of anthelmintic agent, e.g. morantel, to said sac, on pasture land early in the season; i.e., when larval contamination is at or near a minimum level, permits minimization of the usual seasonal increase in larval contamination of the pasture land and serves to protect animals grazing thereon throughout the entire grazing season.

For "indirect control" of helminths, the devices of this invention, preferably in the form of a bolus, are administered to ruminants at a time in the epidemiological cycle of said helminths when pasture contamination by said helminths, their eggs and/or larval stages, is at or near a minimum level. In temperate zones this time corresponds to spring turn out; that is, the first placing (turning out) of the calves out to pasture. For maximum efficiency, the bolus is administered to the calves about two to seven days prior to turning out. In non-temperate zones of the world, e.g. semi-tropical and tropical areas, the period of lowest pasture infectivity normally occurs prior to the rainy season. Administration of the bolus to ruminants in such areas is desirably carried out within two to fourteen days before the start of the rainy season. However, because of the unpredictability as regards the rainy season, helminth control in the non-temperate zones is best achieved by the "direct control" method.

The herein-described boluses also eliminate established helminth infections from ruminants and prevent establishment of worm infections during the summer period of heavy challenge. This mode of use is called "direct control". The direct method of control protect ruminants only during the period of release of the anthelmintic agent. The indirect method of helminth control protects ruminants grazing on a given pasture for the entire season because it achieves an overall significant reduction in pasture contamination.

As noted, the devices described herein provide continuous release, at a controlled rate, of drugs including anthelmintics. Particularly useful for such purposes are water soluble salts of (E)-1,4,5,6-tetrahydro-1-methyl-2-[2-(3-methyl-2-thienyl)ethenyl]]pyrimidine (morantel), (E)-1,4,5,6-tetrahydro-1-methyl-2-[2-(2-thienyl)ethenyl] pyrimidine (pyrantel) and ($\pm$)-2,3,5,6-tetrahydro-6-phenylimidazo[2,1-b]thiazole (tetramisole) and levamisole, the L-($-$)-form thereof. Representative of preferred water soluble salts of pyrantel and morantel are the tartrate and citrate salts; and of tetramisole and levamisole, the hydrochloride salts.

The boluses of this invention are orally administered to animals by, for example, a balling gun. For use in calves, the desirable average release rate of morantel (calculated as base) for indirect control of helminths is on the order of 60–200 mg. (of morantel base) per day for a period of about 60 days, which covers the normal maximum survival time of the spring population of larvae. Longer release periods of from 60–120 days are desirable in the direct control mode of use since the period of exposure to heavy pasture contamination normally extends from mid-summer through autumn. Release rates of about 60–150 mg. (calculated as morantel base) per day effectively control helminth infections over such release periods. For dosing larger animals, more than one bolus can be administered.

Continuous, low-level administration of morantel by use of the herein described devices for helminth control gives rise to an efficacy profile surprisingly different from and advantageous to that observed on conventional therapeutic use of morantel and which could not be predicted. For example, maintenance of a protracted level of morantel tartrate or citrate (or other salt) in the gastrointestinal tract of ruminants is effective in preventing lung worm infections in said animals during the period of drug release. Further, while cattle or sheep grazing on contaminated pasture are subject to immediate reinfection by intestinal nematodes after conventional therapeutic dosing, animals receiving the bolus are essentially freed of established infection and protected from reinfection over a period of 60 days or longer.

The use of the bolus for control of pasture contamination, i.e. the indirect control method, is a unique, practical and unprecedented method of helminth control which protects ruminants, and in particular grazing ruminants, treated via this mode for the entire grazing season and affords performance benefits superior to prior art control methods. The increase in daily weight gain over untreated controls over the grazing season is two or more times that obtained after conventional therapy.

The rate of release of drug, or other chemical, passing from the drug-containing reservoir through the wall of controlled release devices of this invention, and the effectiveness of a given drug and/or water-soluble excipient and/or detergent combination in said devices, can readily be determined by those skilled in the art, for example, by transmission methods, or by sorption-desorption methods. A technique which can conveniently be used to select suitable porous materials and hydrogels comprises using the chosen porous material, pores of which are filled with the selected hydrogel, as a barrier between a rapidly stirred saturated solution of a drug or other chemical, the controlled release of which is desired, and a rapidly stirred solvent bath, the composition of which stimulates the aqueous liquid containing environment in which the controlled release device is to be used. The temperature of each solution is maintained at a constant value, preferably at a value approximating the average temperature of the environment in which said device will be used. Samples are withdrawn at predetermined intervals from the solvent bath and analyzed for drug concentration. Standard procedures for determining the permeability of a drug, or other chemical substance, through the porous material, pores of which are filled with hydrogel, can also be determined by standard procedures as are described in *Encyclopedia of Polymer Science and Technology,* Vols, 5 and 9, pages 65–82 and 794–807, 1968, respectively; and references cited therein; and in *Chemical Engineers Handbook,* pages 17–45, 1963, published by McGraw-Hill, Inc.

A procedure of especial value in determining the release rate for devices of this invention and the relative merits of a given excipient or detergent for use in a given device, particularly wherein the drug is morantel, in summary, is as follows. The procedure, an in vitro procedure, is based upon the release of a water-soluble salt of morantel, for example the tartrate, from a device made in accordance with this invention as a function of time. A morantel tartrate containing device of this invention is placed into a one-liter conical flask which is protected from light because of the photosensitivity of morantel tartrate, 500 ml. of pH 7 phosphate buffer added, and the temperature of the flask and contents adjusted to and maintained at 37° C. The flask containing the device is shaken at about 70 excursions (7.62 cm.) per minute and 5 ml. samples are withdrawn periodically. The volume of the withdrawn sample is replaced with an equivalent volume of fresh pH 7 phosphate buffer and shaking of the flask continued. The concentration of morantel in the samples is determined spectrophotometrically by measuring the absorbance of the sample at 318 nm when read against fresh pH 7 phosphate buffer. The sampling process is repeated until 5 grams of morantel tartrate have been released at which point the device is transferred to another flask containing 500 ml. of fresh pH 7 phosphate buffer and the process continued as before.

In vivo release of morantel tartrate from devices according to this invention is determined by administering the devices to, for example, normal steers or steers with rumen fistula and, after a certain period of time such as 30, 60, 90 or 120 days, removing the devices via the fistule or sacrificing the animals and recovering the devices to determine the residual morantel tartrate within the device. Tests of this sort have shown that the rate of release of morantel tartrate in vitro is approximately four times that of the in vivo release rate.

The following examples are merely illustrative of the present invention. They are not to be construed as limiting the scope of this invention, many variations of which are possible as those skilled in the art will recognize.

EXAMPLE 1

Boluses were prepared from stainless steel tubes having the following dimensions: 22.225 mm. O.D. (⅞ inch), 21.336 mm. I.D. (wall thickness=0.889 mm.≡0.035 inch) and 3 cm. long. The ends of the tubes were threaded (0.5 mm. at each end) to receive a collar which serves to hold a hydrogel impregnated porous fabric disc in place. The discs (22.225 mm. O.D. and 3.175 mm., ⅛ inch thick), polypropylene filter cloth having pores of 50 micron average size and impregnated with gelled cellulose triacetate, were prepared by immersing them in a 6% solution of cellulose triacetate in formic acid contained in a vessel that could be subjected to a vacuum of 25 mm. mercury or less. The flask and contents were held under vacuum for about 10 minutes, the discs removed, and wiped free of excess cellulose triacetate solution. They were then immersed in and allowed to equilibrate in distilled water overnight. The discs were then removed from the water, dried with a towel and then equilibrated with polyethylene glycol 400 overnight. The discs were removed and wiped with a towel.

Impregnated discs were mounted on one end of each of the tubes by sandwiching them between two washers, 0.254 mm (0.01 inch) thick and of the same diameters as the steel tube. The washer adjacent to the steel tube was of cellulose acetate butyrate and the other of dental dam gum rubber. The ends were then capped with stainless steel collars having an opening 21.336 mm. in diameter. The tubes were then filled with morantel tartrate (63.3%), polyethylene glycol 400 (26.6%), sodium hexametaphosphate (10.1%) and the other end of each tube sealed as described above.

The boluses contained 21.4 g. of morantel tartrate, weighed 97 g. and had a mean density of 3.30 g./ml.

The boluses were administered to steers with rumen fistula by use of a balling gun and were removed via the fistule at intervals of 30, 45, 60, 75 and 90 days, to determine the amount of drug remaining in the bolus, from which the mean daily release rate of morantel tartrate was calculated.

| Bolus | Days in Steer | Release Rate (mg./day) |
| --- | --- | --- |
| 1 | 30 | 67 |
| 2 | 30 | 108 |
| 3 | 45 | 82 |
| 4 | 45 | 58 |
| 5 | 60 | 136 |
| 6 | 60 | 91 |
| 7 | 75 | 71 |
| 8 | 75 | 68 |
| 9 | 90 | 67 |
| 10 | 90 | 106 |

The mean release rate was 85 mg./day with a standard deviation of 25 mg.

In each steer significant reduction in fecal parasite egg count was observed.

EXAMPLE 2

The procedure of Example 1 is repeated but using, in place of poly(propylene) filter cloth impregnated with gelled cellulose triacetate, the following gelled cellulose triacetate porous fabrics:

| Porous Fabric | Average Pore Size |
| --- | --- |
| poly(ethylene) | 75 μ |
| poly(tetrafluoroethylene) | 100 μ |
| glass | 60 μ |
| stainless steel filter cloth | 80 μ |
| copper screen | 30 μ |
| modacrylic fiber[a] | 10 μ |
| nickel-copper alloy screen[b] | 50 μ |

[a] copolymer of acrylonitrile (40%) and vinyl chloride(60%), sold under the trademark Dynel by Union Carbide Corp., N. Y.
[b] sold under the trademark Morel by The International Nickel Co., Inc., N. Y.

EXAMPLE 3

Boluses are prepared according to the procedure of Example 2 and the reservoirs filled with the following: morantel citrate (63.3%), polyethylene glycol 400 (26.6%), sodium hexametaphosphate (10.1%) oxantel hydrochloride (100%) morantel citrate (100%) tetramisole hydrochloride (100%) poloxalene (100%) levamisole hydrochloride (85%), glycerol (15%) ampicillin sodium salt (63.5%), polyethylene glycol 400 (26.5%), sodium hexametaphosphate (10.0%) neomycin complex (68.5%), dimethylsulfoxide (22.5%), sodium lauryl sulfate (10.0%) doxycycline hemihydrate hemialcoholate (100%) tylosin hydrochloride (100%) pyrantel citrate (63.6%), glycerol (26.3%), sodium lauryl sulfate (10.1%) bambermycin (100%) sodium penicillin G (67.3%), N,N-dimethylformamide (22.2%), sodium glyceryl monolauryl sulfate (10.5%).

EXAMPLE 4

Four boluses comprising polyethylene filter cloths (average pore size 80μ) pores of which are impregnated with gelled cellulose triacetate, and having stainless steel sleeves within only a portion of the overall length of the boluses (so as to leave a segment of bolus free of sleeve), and reservoirs containing morantel citrate (63.3%), admixed with polyethylene glycol 400 (26.6%) and sodium hexametaphosphate (10.1%) are prepared as follows.

Polyethylene filter cloth (average pore size 80μ) is snugly wrapped around a rod 22.225 mm. (⅞ inch) in diameter so as to provide a single layer. The cloth is then formed into a tube while still in the rod by thermal bonding at the point of overlap of the filter cloth. Excess cloth is cut off. Removal of the rod gives a polyethylene filter cloth tube which is cut into 7.62 cm. lengths (3 inches) each of which is impregnated with gelled cellulose triacetate according to the procedure of Example 1. Stainless steel sleeves or tubes having lengths of 5.08 cm., 4.445 cm., 3.175 cm. and 1.905 cm., respectively, and an O.D. of 22.225 mm. are used. The walls of the sleeves are 0.165 cm. thick. A stainless steel sleeve is inserted into each of the impregnated polyethylene filter cloth tubes so as to be flush with one end thereof. Said end is dipped into a 10% solution of cellulose acetate butyrate in methylene chloride to a depth of 4.763 mm. (3/16 inch). It is then dried in air and the step is repeated. It is again dipped into the cellulose acetate butyrate solution for 30 seconds, allowed to dry in air for 60 seconds, and a 22.225 mm. (⅞ inch) cellulose acetate butyrate disc (3.175 mm. thick) inserted into the end of the tube so as to be flush with said end. The cellulose acetate butyrate disc is floated on methylene chloride for 60 seconds prior to its insertion into said end of the tube. The tube is then rolled along the bench, applying finger pressure to the end thereof containing the disc, so as to insure complete binding of disc and tube. Drug mix is then loaded into each bolus so as to provide a drug-band width of 6.35, 12.70, 25.4 and 38.1 mm., respectively above the sleeves. A stainless steel plug, 12.7 mm. thick and 22.225 mm. diameter, is inserted into each of the boluses above the drug mixture. The ends of the boluses bearing the steel plug are trimmed so as to permit insertion of a cellulose acetate butyrate disc by the procedure described above on top of the plugs and flush with the ends of the boluses.

EXAMPLE 5

In vitro tests of the release rate of morantel citrate by the boluses of Example 4 shows each of them affords constant release of morantel citrate over a period of 3–21 days.

EXAMPLE 6

Boluses are prepared according to the procedure of Example 4 but using, in place of the drug mixture of said Example, the following chemicals in the reservoir: pyrantel tartrate (63.3%), polyethylene glycol 400 (26.6%), sodium hexametaphosphate (10.1%); morantel tartrate (100%); pyrantel hydrochloride (100%); tetramisole hydrochloride (100%); levamisole hydrochloride (85.0%), glycerol (15.0%), diethylcarbamazine citrate (100%); hydromycin B (100%); doxycycline hemihydrate hemialcoholate (100%); bacitracin methylenedisalicyclic acid (66.0%), sorbitol (22.0%), sodium lauryl sulfate (12.0%); ampicillin, sodium salt (63.5%), polyethylene glycol (26.5%), sodium hexametaphosphate (10.0%); sodium penicillin G (67.3%), N,N-dimethylformamide (22.2%), sodium glyceryl monolauryl sulfate (10.5%); neomycin complex (68.5%), dimethylsulfoxide (22.5%), sodium lauryl sulfate (10.0%); streptomycin trihydrochloride (100%); oleandomycin hydrochloride (80%), polyethylene glycol 400 (20%); tylosin hydrochloride (100%), polymyxin hydrochloride (79.5%), glycerol (15.0%), sodium lauryl sulfate (5.5%); lincomycin hydrochloride hemihydrate (100%); magnesium acetate tetrahydrate (77%), sorbitol (15%), dioctyl disodium sulfosuccinate (8%).

EXAMPLE 7

The procedure of Example 1 is repeated but using the following chemicals in the reservoir: pyrantel citrate (100%); tetramisole hydrochloride (71.8%), propylene glycol (18.2%), sodium tripolyphosphate (10.0%); avoparicin hydrochloride (100%); oxantel hydrochloride (63.2%), polyethylene glycol 400 (26.3%), sodium lauryl sulfate (10.5%); 5-oxytetracycline hydrochloride (100%); apramycin trihydrochloride (100%); bambermycin (63.3%), glycerol (24.5%), sodium lauryl sulfate (12.2%); piperazine hydrochloride (100%); amprolium hydrochloride (100%); poloxalene (100%); thiamine hydrochloride (100%).

EXAMPLE 8

A bolus comprising polypropylene (average pore size 30μ) pores of which are filled with a cross-linked polyvinyl alcohol hydrogel, and a reservoir containing morantel citrate (63.3%), polyethylene glycol 400 (26.6%) and sodium hexametaphosphate (10.1%), and having a stainless steel sleeve is prepared according to the procedure of Example 1. In place of the cellulose triacetate-formic acid solution, however, the hydrogel solution comprises an aqueous solution of 10% polyvinyl alcohol (88% hydrolyzed polyvinyl acetate) containing 3% resorcinol. The discs, following vacuum treatment to fill their pores, are wiped clean and held at 0° C. to −10° C. for 5 hours to gel the polymer. Equilibration of the tube in water is unnecessary. The tube is then equilibrated in polyethylene glycol 400, filled and sealed as in Example 1.

In vitro testing shows it affords controlled release of morantel citrate over a prolonged period of time.

Repetition of this procedure but using nylon discs (average pore size of 60μ) also affords a bolus which provides for controlled release of morantel citrate over a prolonged period of time.

EXAMPLE 9

Boluses are prepared according to Example 1 but using stainless steel filter cloth discs (average pore size 80μ) impregnated with gelled cellulose triacetate in place of polypropylene impregnated discs. The reservoirs are filled with the following: 5-oxytetracycline hydrochloride (100%); ampicillin sodium salt (63.5%), polyethylene glycol 400 (26.5%), sodium hexamethaphosphate (10%); doxycycline hemihydrate hemialcoholate (100%); bacitracin methylene dialicyclic acid (66.0%), sorbitol (22%), sodium lauryl sulfate (12.0%); tylosin hydrochloride (100%); lincomycin hydrochloride (100%); erythromycin hydrochloride (100%).

Each bolus affords controlled release of its respective drug upon in vitro tests in water as the environment.

EXAMPLE 10

An envelope shaped device (3 cm.×2 cm.×0.5 cm.) is made by folding a 3 cm.×7 cm. piece of polyethylene cloth (average pore size 100μ), previously impregnated with gelled cellulose triacetate according to the procedure of Examole 1, lengthwise. The two open ends extending from the fold are double stitched with polyethylene thread 0.5 cm. from each end. The sides are then folded over at the stitching and the folds double stitched with polyethylene thread. The envelope is then filled with N-tritylmorphine to within 0.5 cm. of the open end with sufficient chemical to give an envelope 0.5 cm. thick. The open end is then folder over and double stitched with polyethylene thread.

The device when tested in vitro by placing it in a flask containing 500 ml. water and shaking said flask at 37° C. and about 70 excursions (7.62 cm.) per minute is found to afford substantially constant release of N-tritylmorphine. The procedure comprises withdrawing 5 ml. samples from the flask periodically and replacing the withdrawn sample with an equivalent volume of water. The concentration of N-tritylmorphine is determined by appropriate means, e.g. spectrophotometrically.

EXAMPLE 11

Boluses are prepared from stainless steel tubes having the following dimensions: 22.225 mm. O.D. (⅞ inch), 21.336 mm. I.D. (wall thickness=0.889 mm.×0.035 inch) and length 7.62 cm. (3 inches). The ends of the tubes are threaded (0.5 mm. at each end) to receive a collar which serves to hold a porous, hydrogel impregnated disc in place. The discs (22.225 mm. O.D. and 3.175 mm. thick), polypropylene filter cloth (50 micron average pore size) impregnated with gelled cellulose triacetate, are prepared by immersing them in a 6% solution of cellulose triacetate in acetic acid contained in a vessel that can be subjected to a vacuum of 25 mm. mercury or less. The flask and contents are held under vacuum for about 10 minutes, the discs removed, and wiped free of excess cellulose triacetate solution. They are then immersed in and allowed to equilibrate in distilled water overnight. The discs are then removed from the water, dried with a towel and then equilibrated with polyethylene glycol 400 overnight. The discs are removed and wiped with a towel.

Impregnated discs are mounted on one end of each of the tubes by sandwiching them between two washers, 0.254 mm. (0.01 inch) thick and of the same diameters as the steel tube. The washer adjacent to the steel tube is of cellulose acetate butyrate and the other of dental dam gum rubber. The ends are then capped with stainless steel collars having an opening 21.336 mm. in diameter. The tubes are then filled with the desired chemicals and the other end of each tube sealed as described above.

Tubes (boluses) having the following chemicals in the reservoir are thus prepared: morantel citrate (63.3%), polyethylene glycol 400 (26.6%), sodium hexametaphosphate (10.1%); oxytetracycline hydrochloride (100%); pyrantel citrate (88%), glycerol (12%); pyrantel tartrate (63.3%), polyethylene glycol 400 (26.6%), sodium lauryl sulfate (10.1%); tetramisole hydrochloride (100%); poloxalene (100%); erythromycin hydrochloride (100%); thiamine hydrochloride (100%).

What is claimed is:

1. A device for the controlled and continuous administration of a chemical to an aqueous liquid-containing environment over a prolonged period of time, said device comprising a reservoir containing said chemical, a shaped wall formed in part at least of a porous fabric material, said porous fabric material being in contact with at least a part of said reservoir and being insoluble in said environment while maintaining its integrity during said prolonged period of time, and a hydrogel medium means impregnating the pores of said porous fabric material, said hydrogel medium means having channels or pores which (1) permit the diffusion of aqueous liquid from said environment into said reservoir to form a solution of said chemical in said aqueous liquid and (2) permit the diffussion of said solution containing said chemical to said environment, the dissolved chemical so released being replaced by the continuous dissolving of said chemical in said reservoir and the amount of dissolved chemical in said reservoir changing continuously throughout said prolonged period of time so as to maintain the rate of chemical release to said environment substantially constant during a substantial portion of said prolonged period of time.

2. A device according to claim 1 wherein the reservoir contains chemical in admixture with a water-soluble excipient.

3. A device according to claim 1 wherein the reservoir contains chemical in admixture with a water-soluble liquid excipient and a detergent.

4. A device according to claims 1 or 2 wherein said porous fabric material selected from the group consisting of poly(ethylene), poly(propylene), poly(tetrafluoroethylene), glass, nylon, cotton, and modacrylic.

5. A device according to claims 1 or 2 wherein the aqueous liquid containing environment is an animal body site.

6. A device according to claim 5 wherein the animal body site is the rumeno-reticular sac of a ruminant.

7. A device according to claim 6 wherein the hydrogel medium is gelled cellulose triacetate.

8. A device according to claim 2 wherein the chemical is an anthelmintic agent.

9. A device according to claim 8 wherein the chemical is a water soluble acid addition salt of pyrantel, morantel or levamisole.

10. A device according to claim 9 wherein the water soluble acid addition salt is selected from the group consisting of levamisole hydrochloride and the tartrate and citrate salts of morantel and pyrantel.

11. A device according to claim 10 wherein the chemical is a water soluble acid addition salt of morantel.

12. A device according to claim 11 wherein the porous material is polypropylene and the water soluble salt is the tartrate.

13. A device according to claims 1 or 2 wherein said device contains a high density material in such quantity that the device has a density of at least 2.0.

14. A device according to claim 13 wherein the porous fabric material is selected from the group consisting of poly(ethylene), poly(propylene), poly(tetrafluoroethylene), glass, nylon, cotton, and modacrylic.

15. A device according to claim 14 wherein said high density material is steel and the shaped wall comprises a cylinder of said steel, the ends of which are sealed with a porous fabric material, pores of which contain gelled cellulose triacetate.

16. A device according to claim 14 wherein said high density material is present as a perforated steel sleeve within said device between the reservoir and the porous fabric material.

17. A device according to claim 15 wherein the porous fabric material is poly(propylene) and the hydrogel is gelled cellulose triacetate.

18. A device according to claim 17 wherein the aqueous liquid-containing environment is the rumeno-reticular sac of a ruminant.

19. A device according to claim 18 wherein the chemical is a water soluble salt of morantel.

20. A device according to claim 19 wherein the water soluble salt is the citrate salt.

21. A device according to claim 19 wherein the water soluble salt is the tartrate salt.

22. A method for the control of helminthiasis in ruminant animals which comprises administering to said animals for retention in the rumeno-reticular sac, a device for the controlled and continuous administration of a water soluble salt of morantel to the aqueous liquid-containing environment in said rumeno-reticular sac over a prolonged period of time, said device comprising a reservoir containing said morantel, a shaped wall formed in part at least of a porous fabric material, pores of which contain a hydrogel medium, said porous fabric wall to contact with at least a part of said reservoir and characterized by being insoluble in said environment and maintaining its integrity during said prolonged period of time, said hydrogel medium being permeable to passage of said morantel and to said aqueous liquid so that said device when placed in said environment continuously releases said morantel from said reservoir to said environment at a physiologically effective controlled rate through said medium, the dissolved morantel so released being replaced by the continuous dissolving of said morantel in said reservoir, the amount of dissolved morantel in said reservoir changing continuously throughout said prolonged time period, so as to maintain the rate of morantel release to said environment substantially constant during a substantial portion of said prolonged time period.

23. A method according to claim 22 wherein the reservoir contains a water soluble salt of morantel in admixture with a water-soluble excipient.

24. A method according to claim 22 wherein the reservoir contains a water soluble salt of morantel in admixture with a water-soluble liquid excipient and a detergent.

25. A method according to claims 22 or 23 wherein said porous fabric material is selected from the group consisting of poly(ethylene), poly(propylene), poly(tetrafluoroethylene), glass and modacrylic.

26. A method according to claim 25 wherein the hydrogel medium is gelled cellulose triacetate.

27. A method according to claim 26 wherein the water soluble acid addition salt of morantel is selected from the group consisting of the tartrate and citrate.

28. The method according to claim 27 wherein the porous material is polypropylene and the water soluble salt is the tartrate.

29. The method according to claim 27 wherein the porous material is polypropylene and the water soluble salt is the citrate.

30. A method according to claims 22 or 23 wherein said device contains a high density material in such quantity that the device has a density of at least 2.0.

31. A method according to claim 30 wherein the porous fabric material is selected from the group consisting of poly(ethylene), poly(propylene), poly(tetrafluoroethylene), glass, nylon, cotton, and modacrylic.

32. A method according to claim 31 wherein the porous material is poly(propylene).

33. A method according to claim 32 wherein the hydrogel is gelled cellulose triacetate.

34. The method according to claim 33 wherein the water soluble salt is the citrate salt.

35. The method according to claim 33 wherein the water soluble salt is the tartrate salt.

36. A method for the control of helminths on pasture land, the helminth larval contamination of which is at or near a minimum level, which comprises grazing on said land, ruminant animals having in their rumeno-reticular sacs a device for the controlled and continuous administration of a water soluble salt of morantel to the aqueous liquid-containing environment in said rumeno-reticular sac over a prolonged period of time, said device comprising a reservoir containing said morantel, a shaped wall formed in part at least of a porous fabric material, pores of which contain a hydrogel medium, said porous wall in contact with at least a part of said reservoir and characterized by being insoluble in said environment and maintaining its integrity during said prolonged period of time, said hydrogel being permeable to passage of said morantel and to said aqueous liquid so that said device when placed in said environment continuously releases said morantel from said reservoir to said environment at a physiologically effective controlled rate through said medium, the dissolved morantel so released being replaced by the continuous dissolving of said morantel in said reservoir, the amount of dissolved morantel in said reservoir changing continuously throughout said prolonged time period, so as to maintain the rate of morantel release to said environment substantially constant during a substantial portion of said prolonged time period.

37. A method according to claim 36 wherein the wall of said device comprises a steel cylinder, the ends of which are sealed with polypropylene, pores of which contain gelled cellulose triacetate.

38. A method for the control of lung worm infections in ruminant animals which comprises administering to said animals for retention in the rumeno-reticular sac, a device for the controlled and continuous administration of a water soluble salt of morantel to the aqueous liquid-containing environment in said rumeno-reticular sac over a prolonged period of time, said device comprising a reservoir containing said morantel, a shaped wall formed in part at least of a porous fabric material, said porous fabric wall in contact with at least a part of said reservoir and characterized by being insoluble in said environment and maintaining its integrity during said prolonged period of time, said hydrogel medium being permeable to passage of said morantel and to said aqueous liquid so that said device when placed in said environment continuously releases said morantel from said reservoir to said environment at a physiologically effective controlled rate through said medium, the dissolved morantel so released being replaced by the continuous dissolving of said morantel in said reservoir, the amount of dissolved morantel in said reservoir changing continuously throughout said prolonged time period, so as to maintain the rate of morantel release to said environment substantially constant during a substantial portion of said prolonged time period.

* * * * *